(12) United States Patent
VanStockum

(10) Patent No.: US 7,368,131 B2
(45) Date of Patent: May 6, 2008

(54) METHOD AND COMPOSITION FOR TREATING HYPOPIGMENTATION OF THE HAIR AND SKIN

(75) Inventor: Audrey VanStockum, Chicago, IL (US)

(73) Assignee: Supernatural Health, Inc., Chicago, IL (US)

( * ) Notice: Subject to any disclaimer, the term of this patent is extended or adjusted under 35 U.S.C. 154(b) by 407 days.

(21) Appl. No.: 10/782,827

(22) Filed: Feb. 23, 2004

(65) Prior Publication Data

US 2004/0170702 A1    Sep. 2, 2004

Related U.S. Application Data

(60) Provisional application No. 60/449,866, filed on Feb. 27, 2003.

(51) Int. Cl.
| | |
|---|---|
| *A61K 33/34* | (2006.01) |
| *A61K 33/32* | (2006.01) |
| *A61K 31/70* | (2006.01) |
| *A61K 31/34* | (2006.01) |
| *A01N 59/20* | (2006.01) |
| *A01N 59/16* | (2006.01) |
| *A01N 43/04* | (2006.01) |
| *A01N 43/08* | (2006.01) |

(52) U.S. Cl. ............... 424/638; 424/630; 424/641; 514/52; 514/168; 514/474; 514/904

(58) Field of Classification Search ............... 424/630, 424/641; 514/52, 168, 258.1, 474, 904
See application file for complete search history.

(56) References Cited

U.S. PATENT DOCUMENTS

| | | | |
|---|---|---|---|
| 4,507,277 A | 3/1985 | Cao | |
| 4,985,443 A | 1/1991 | Montes | |
| 5,049,547 A | 9/1991 | Hruby | |
| 5,750,091 A | 5/1998 | Gilchrest | |
| 5,942,531 A | 8/1999 | Diaz | |
| 6,013,279 A * | 1/2000 | Klett-Loch | 424/451 |
| 6,143,723 A | 11/2000 | Ramaiah | |
| 6,149,933 A | 11/2000 | Nelson | |
| 2001/0044422 A1 | 11/2001 | Zhao | |

FOREIGN PATENT DOCUMENTS

RU        2163486        3/2000

OTHER PUBLICATIONS

Kelly, GS. Alternative Medicine Review 1997, 2(2), pp. 116-127.*
MedlinePlus Medical Encyclopedia: vitiligo Jul. 2, 2004 pp. 1-2.*
MedlinePlus Medical Encyclopedia: albinism Mar. 13, 2006 p. 1-3.*
Randic et al. Biology of Reproduction 1973, 8, 495-498.*
American Association of Naturopathic Phsycians, Nature's Pharmacy, Publications International, Ltd., 1998, pp. 203-205; 209-222; 235-236.
Bagnara, Joseph T., Advances in Pigment Cell Research, Alan R. Liss, Inc., NY, 1988, pp. 195-206; 225; 463-474.
Balch, James F., M.D., Phyllis A. Balch, C.N.C., Prescription for Nutritional Healing, Avery Publishing Group, Inc., Garden City Park, NY, 1990, pp. 6-9.
Clark, Linda, Know Your Nutrition, Keats Publishing, Inc., New Canaan, CT, 1973, pp. 100-108; 115-125.
Clark, Linda, Secrets of Health and Beauty, The Devin-Adair Company, Old Greenwich, 1970, pp. 202-207.
Glass, George B. Jerzy, Gastric Intrinsic Factor and other Vitamin B12 Binders, Georg Thieme Publishers Stuttgart, 1974, pp. 61-95.
Hendler, Sheldon Saul, The Doctor's Vitamin and Mineral Encyclopedia, Simon and Schuster, NY, 1990, p. 74.
Howell, John, Copper in Animals and Man, vol. II, CRC Press, Inc., Boca Raton, FL, 1987, p. 21; 32.
Linder, Maria C., Biochemistry of Copper, Plenum Press, NY, 1991, pp. 231-235.
Micromedex, Hydrochloric Acid, http://www.healthyroads.com/mylibrary/data/altcaredex/htm/ame0288.asp?HP=&.
Montes, Leopoldo F., "Folic Acid and Vitamin B12 in Vitiligo: A Nutritional Approach," Cutis (magazine), vol. 50, Jul. 1992; pp. 39-42.
Montes, Leopoldo F., Vitiligo, Nutritional Therapy, Westhoven Press, Buenos Aires, 1999, pp. 115-144; 163-176.
Nordlund, James J., The Pigmentary System, Oxford University Press, NY, 1998, pp. 407-411.
Ortonne, Jean-Paul, Vitiligo and Other Hypomelanoses of Hair and Skin, Plenum Medical Book Co., NY, 1983, pp. 1-7; 15-20; 26-28; 102-103.
Owen, Charles A., Jr., Physiological Aspects of Copper, Noyes Publications, Park Ridge, NJ, 1982, pp. 208-213.
Picciano, Mary Frances, Folic Acid Metabolism in Health and Disease, Wiley-Liss, 1990, pp. 12-13.
Riley, Vernon, Pigmentation, Appleton-Century Crofts, NY, 1972, pp. 445-450.
Sebrell, W.H., Jr., The Vitamins, vol. 1, Academic Press, NY, 1967, pp. 457-485.
Sebrell, W.H., Jr., The Vitamins, vol. II, Academic Press, NY, 1967, pp. 220-242.
Jimbow, K., Vitiligo Therapeutic Advances, Dermatalogic Clinics, London, Apr. 1998, 16(2), pp. 399-407.
Kolyandenko, V.G., et al., Application of Copper-and-Zinc-Containing Adsorbents in Complex Vitiligo Treatment, International Journal of Artificial Organs, Aug. 2000, 23(8), p. 568.
Juhlin, L., et al., Improvement of Vitiligo After Oral Treatment with Vitamin B12 and Folic Acid and the Importance of Sun Exposure, Acta Dermato-Venereologica, Nov. 1997, 77(6), pp. 460-462.
Somyos, K., et al., Copper Vapour Laser Treatment of Café-au-Lait Macules, British Journal of Dermatology, 1996, 135(6), pp. 964-968.

* cited by examiner

*Primary Examiner*—Johann Richter
*Assistant Examiner*—Ernst V Arnold
(74) *Attorney, Agent, or Firm*—Kramer & Amado, P.C.; Arlir M. Amado; Terry W. Kramer

(57) ABSTRACT

A method of treating disorders marked by a loss of pigmentation, comprising the step of administering vitamin B12, copper, folic acid, and vitamin C to a patient suffering from a loss of pigmentation. Additionally, an effective amount of both pantothenic acid and zinc may be administered to the patient. Cutaneous repigmentation can be accelerated by the optional addition of exposure to sunlight or ultraviolet light.

21 Claims, No Drawings

METHOD AND COMPOSITION FOR TREATING HYPOPIGMENTATION OF THE HAIR AND SKIN

This application claims priority to U.S. Provisional Application 60/449,866, filed Feb. 27, 2003.

FIELD OF THE INVENTION

This invention generally relates to a dietary supplement, which is useful for pigment restoration in the skin and hair of human subjects. The use of the present dietary supplement can reverse the loss of pigmentation in the skin and hair, resulting from such conditions as vitiligo. Thus, at least for some individuals, the natural skin or hair color can be restored, and maintained, naturally without the use of cosmetics or of medical procedures.

BACKGROUND OF THE INVENTION

The coloration of human skin is determined principally by the concentration of melanin produced by the melanocytes. The melanocytes are specialized cells, which synthesize melanin by means of specific organelles, the melanosomes. The same holds true for the coloration of hair on the head and body, as well as the fingernails and toenails. Medical disorders which cause a loss of these melanocytes can result in diseases, such as vitiligo, marked by a loss of skin pigmentation.

Vitiligo affects 1%-2% of the world population, and results from a lack of melanin in the epidermis due to the disappearance of melanocytes from the skin. Clinically, the patients display white areas of various sizes and shapes, either localized or generalized. Frequently, these white areas have a symmetrical distribution on both halves of the body. Vitiligo can begin at any age and become gradually progressive to the point of affecting the entire skin. Although the precise cause of vitiligo is not known, such clinical behavior speaks in favor on an internal or systemic etiology. It is possible that vitiligo is an autoimmune condition. Studies have reported that patients with vitiligo exhibit a circulating autoantibody that binds to melanocytes in human skin, nevus cells and melanoma cells.

Despite extensive therapeutic efforts over the years, the treatments available are unsatisfactory, to say the least. W. B. Shelley, the great master of American Dermatology, has summarized the drama and frustration in the management of this disease, particularly in the darker skin, as follows: "the vitiliginous areas of the face are truly disfiguring. Years ago Nehru recognized this fact by ranking the need for a treatment of vitiligo on a level with that for leprosy and tuberculosis. In all instances there is a quest for help. At present the best we can offer is little. Surely in this century of moon flights, we should be able to do better . . . " (W. B. Shelley, "Consultations in Dermatology", W. B. Saunders, Philadelphia, 1972).

Various solutions have been proposed to the art of artificial coloration by applying dyes that are intended to color the skin and or hair to match as close as possible its natural color or in the field of natural coloration via stimulation of the natural pigmentation pathways or in the field of decoloration by depigmenting the skin. Good results have been obtained with some negative side effects. A number of methods of treating skin depigmentation are available; while some are effective to a greater or lesser degree, most have some drawbacks. One such method involves the use of pseudocatalese cream (PCAT), which should be applied twice daily. PCAT contains calcium chloride, manganese chloride, sodium bicarbonate, and distilled water. PCAT inhibits the progression of pigment loss, and reduces skin levels of peroxides which are known to be increased in vitiligo patients. However, there are certain drawbacks to PCAT. First, the cream can cause skin to break out in pimples and cause ingrown hairs. Also, patients should be screened for phenylalanine deficiency first as PCAT is more effective for people with phenylalanine deficiency.

Novitil, which works as a tanning accelerator, has also been tried as a vitiligo treatment. This is a formulated gel containing oils, distilled water, glycerin, carboxymethylcellulose, camphor, menthol, polypeptides, Aloe Barbadensis, oligoelements and kathon (a preservative), which is used in conjunction with exposure to the sun or a sun lamp for it to work. Sinvitil, an earlier version of Novital which did not include the polypeptides, Aloe Barbadensis, and oligoelements, has also shown promise in repigmentation therapy. However, these gels must be left on for at least two hours after treatment, significantly restricting the patient's mobility.

Another topical treatment is V-Tar, a 30% standardized water soluble coal tar product which also contains natural anti-inflammatory agents, skin conditioners, and antioxidants. V-Tar has been used successfully in many patients with vitiligo and other hypopigmentary disorders. It will not stain the skin, and its once weekly application is convenient for many patients. V-Tar is available only with a physician's prescription.

Other topical treatments include the use of steroid creams or immunomodulators. Application of steroid creams to white patches of vitiliginous skin for three months can aid in skin repigmentation; however, this treatment can cause thinning of the skin, blood vessel formation, steroid induced acne, atrophy, joint problems, and possibly arthritis. In theory, topical immunomodulators alter the immune response to the skin, curbing the immune response in vitiliginous skin. The ointment Protopic is such an immunomodulator. Those who have tried protopic report burning and itching as side effects. Although Protopic has been approved by the FDA for eczema, the FDA does not support the clinical investigation or use of Protopic for vitiligo at this time.

PUVA, a phototherapy treatment involving use of psoralen, in conjunction with ultra violet A (UVA) light is another common treatment. In one frequently-used regimen, oral doses of psoralen are taken two hours before exposure to UVA light or to sun light. Normally, the patient wears wraparound sunglasses to protect his or her eyes. Alternatively, topical psoralen therapy, in which psoralen is applied to skin 30 minutes before exposure to UVA light until white, vitiliginous skin turns pink, may be used. These treatments, however, have significant side effects, including sunburn, redness, blistering, and inflammation. PUVA treatments are not recommended for children under age 10 because phototherapy can cause eye damage and cataracts. Oral psoralen can also cause severe stomach upset, gastrointestinal upset, nausea, and liver toxicity. Phototherapy with psoralen has also been linked to some forms of cancer, including non-melanoma skin cancer. In the case of oral psoralen, the patient must avoid sunlight for 12-24 hours after treatment. The patient must wear special sunglasses for two hours following treatment. Maintenance treatments are required to see continued improvement.

Narrow band UVB or excimer laser treatment of vitiliginous skin consists of highly concentrated beams of narrow band UV light. This procedure maximizes delivery of narrow band UVB radiation to the tissue requiring treatment, while minimizing exposure to superfluous UV radiation. However, this form of phototherapy can also cause burning, like PUVA. This sunburn is less severe than other forms of UV light, but it is not safe around the eyes. Some patients have, however, reported significant success.

In particularly severe cases of vitiligo, where the patches of white skin cover large parts of the body surface, depigmentation is sometimes used. In this therapy, the drug monobenzylether of hydroquinone (monobenzone or Benoquin) is applied to skin twice a day until pigmented skin fades skin fades until it matches the patches of depigmented skin. The patient must avoid skin to skin contact with other people for at least 2 hours after application of the drug. Some patients have allergies to Benoquin, and show contact dermatitis, including inflammation (redness and swelling), rash, itching, and dry skin. The rash, inflammation, and itching have been likened to poison ivy. Depigmentation once completed, leaves the patient extremely sensitive to sunlight. This treatment is, in most cases, permanent.

If desired by the patient, surgical procedures may be explored. These include skin grafting and melanocyte transplant. In skin grafting, pieces of normal skin are removed and placed in white skin patches. Melanocyte transplant involves placement of a sample of normally pigmented skin in a laboratory dish with a solution to grow melanocytes. After the melanocytes have multiplied, they are transplanted into the depigmented skin or depigmented skin of the depigmented hair. Both of these procedures are invasive, and may result in infections, scarring, and/or uneven skin pigmentation.

For patients who prefer to avoid medical or surgical intervention, the condition may be concealed with cosmetics for the skin or dye for the hair. However, these cosmetic treatments do not solve the problem, and need continuous application. Some cosmetics may cause allergic reactions.

Nutritional repigmentation therapies using vitamins and/or minerals known in the art to be safe have been proposed. One such nutritional therapy for vitiligo was described by Montes (U.S. Pat. No. 4,985,443). This therapy involves oral treatment with folic acid, alone or in combination with vitamins C and B12. A second repigmentation therapy, disclosed as useful for treatment of grey hair, but not vitiligo, was proposed by Nelson (U.S. Pat. No. 6,149,933). This treatment regimen involves administration of copper, p-aminobenzoic acid, pantothenic acid, and vitamin B6.

The Nelson and Montes treatments have achieved some good yet inconsistent results. One area their treatments overlook is vitamin and mineral absorption. Some of their test patients did not achieve any results or unsatisfactory results. It is possible that these patients did not absorb (in their digestive systems) the vitamins and minerals.

SUMMARY OF THE INVENTION

There is thus a long-felt need in the art for therapies for treatment of vitiligo which are not prone to the frequently severe side effects of the treatments described above, and which do not require surgical intervention. More particularly, there is a need for further compounds and compositions which are able to stimulate the proliferation of melanocytes. In accordance with the present invention a combination of vitamins and minerals stimulates pigmentation in the skin and hair. Advantages over prior art vitiligo treatments include a lack of dermatological side effects, including allergies, sunburn, scarring, and cancer, as well as a lack of gastrointestinal distress. It does not make the patient sensitive to sunlight, and it does not require exposure to UV light or the sun, although UV exposure may accelerate repigmentation.

The current invention provides a method of treating disorders marked by a loss of pigmentation, comprising the step of administering vitamin B12, copper, folic acid, and vitamin C to a patient suffering from a loss of pigmentation. Additionally, an effective amount of both pantothenic acid and zinc may be administered to said patient. Cutaneous repigmentation can be accelerated by the optional addition of exposure to sunlight or ultraviolet light.

DESCRIPTION OF THE PREFERRED EMBODIMENTS

The present invention is directed to materials and methods for the treatment of depigmented skin and hair. Treatment methodology includes ingestion of a preparation based upon a combination of vitamins and a mineral. In a preferred embodiment, the composition comprises about 0.15-50 mg/day of folic acid; about 0.007-500 mg/day or more of vitamin B12; about 15-1000 mg/day or more of vitamin C; about 0.7-3 mg/day of copper. These may be administered orally every day (every 24 hours). Several optional ingredients may be added to the composition. These optional ingredients include about 1.7-900 mg/day of pantothenic acid. Also, the optional inclusion of about 600-1,800 mg/day of hydrochloric acid is in some cases advisable. Hydrochloric acid may be administered orally in divided doses at mealtimes. Copper can deplete zinc in the body. To offset this, Zinc can optionally be added in the range of 3 to 80 mg. This formulation may be administered for the duration of 3 months to 2 years.

Typically, copper and zinc are administered as a salt or an oxide, such as copper oxide, copper peptides, copper sulfate, copper oxide, copper carbonate, and tribasic copper chloride, zinc oxide, and zinc sulfate. Hydrochloric acid is frequently administered as a salt with trimethylglycine, known as betaine HCl. In particular, Betaine HCl is useful for adequate absorption of protein, calcium, vitamin B12 and iron.

The contemplated treatment regimen may be administered in a number of treatment forms, including tablets, sublingual dosage forms, subcutaneous injections, liquid dosage forms to be swallowed, liquid dosage forms to be sprayed into an oral or nasal cavity, and combinations thereof. For example, folic acid, copper, vitamin C, vitamin B12, pantothenic acid and zinc may be compounded into one tablet that is swallowed. If preferred, folic acid, copper, vitamin C, vitamin B12, pantothenic acid, and zinc may each be taken as separate tablets that are swallowed. Alternatively, folic acid, copper, vitamin C, pantothenic acid and zinc can be compounded into one tablet that is swallowed; and the vitamin B12 being administered in a separate tablet that is taken sublingually, or as a subcutaneous injection. Folic acid, copper, vitamin C, vitamin B12 and pantothenic acid can all be administered subcutaneously, be it in multiple injections or all mixed into one injection. The advantage of subcutaneous administration is that it may require doses to be repeated weekly, rather than daily, making this treatment method potentially more convenient for the patient. If the treatment is administered in tablet form, the tablet may be a chewable tablet, or the tablet may be swallowed whole, or both types of tablets maybe used in conjunction. If desired, for example, vitamin B12 may be administered in a chewable tablet, while the remaining ingredients may be administered in a tablet designed to be swallowed whole.

Tablet formulations may be compounded with a variety of conventional excipients, binders, lubricants and/or fillers. Suitable binders and/or excipients include gelatin, polyvinyl pyrolidone, Acacia Gum, Agar, Cellulose, Microcrystalline Cellulose, alkyl and/or hydroxyalkyl cellulose ethers, cellulose acetate, Modified Cellulose Gum, Guar Gum, Maltodextrin, and Tragacanth Gum. Suitable fillers and/or lubricants include Calcium Stearate, Colloidal Silicon Dioxide, Dibasic Calcium Phosphate, Stearic Acid, Magnesium Stearate, Zinc Stearate, and Simethicone. Sublingual dosage forms typically include a soluble sweetener such as Fructose, Mannitol, Sorbitol, or Xylitol, which dissolves in saliva, allowing release of the active ingredient in the mouth. Sublingual dosage forms may include some of the previously listed excipients, binders, lubricants and fillers.

Folic acid, copper, vitamin C, vitamin B12 and pantothenic acid may be compounded as a soluble powder, and dissolved or dispersed in a pharmaceutically acceptable aqueous medium. This aqueous medium may be a beverage, such as water or juice, which the patient may then drink. Such a beverage may be mixed by the patient at home, or premixed at a manufacturing plant. Alternatively, the powder may be dissolved in an aqueous medium comprising water, along with alcohol or glycols, preservatives, buffers, and/or rheology modifiers, resulting in an aqueous composition useful as a spray that may be sprayed into the oral or nasal cavity. A beverage is believed to be preferable, in that it allows better control of the dosage administered to the patient.

In cases where vitamin B12 is administered orally in tablet form, the efficacy of the formulation is further enhanced by the optional addition of hydrochloric acid or Betaine HCl. This supplement can enhance absorption of vitamin B12 from the stomach and intestine by increasing levels of stomach acid. Low stomach acid, known as hypochlorhydria, interferes with the absorption of B12 from food. Additionally, supplemental use of hydrochloric acid normalizes folic acid absorption and vitamin C, in cases of low or no stomach acid.

In certain cases, women may want to suspend copper intake during their menses. Copper levels are elevated during menses. Taking a copper supplement during this time could lead to copper toxicity. Not all women are susceptible to copper toxicity. If a woman has a low copper level, or is in menopause, copper toxicity is not an issue. If, however, a woman has a high level of copper in her system under normal circumstances, or is also taking another vitamin or mineral supplement including copper, such as complexion vitamins for women by Oil of Olay which contain 2 mg. of copper, the risk of copper toxicity is increased. To avoid this, women may cease repigmentation therapy during menses. As an alternative, women may cease copper supplementation during menses, but continue taking other nutrients. On days when a female patient is not undergoing menses, an effective daily amount of vitamin B12, an effective daily amount of copper, an effective daily amount of folic acid, and an effective daily amount of vitamin C to said female patient may be given; and on days when the female patient is undergoing menses, the treatment regimen may be continued, with the exception that administration of copper is stopped until the cessation of menses. Pantothenic acid, zinc, and, if necessary, HCl may be administered to the female patient on a continuing daily basis.

From the description herein, a number of advantages of the inventive method and treatment of hypopigmentation of the hair and skin will become apparent. Multiple phases of the pigment production process are supported. Thus, pigment production is less likely to fail. Absorption of the active vitamins can be assured and enhanced by the optional addition of hydrochloric acid to the formulation. Cutaneous repigmentation can be accelerated by the optional exposure to sunlight or ultraviolet light. This treatment is helpful for repigmenting depigmented skin and hair (i.e. gray hair).

The current invention is believed to act on a metabolic pathway which converts tyrosine to melanin. Melanin provides protection against ultraviolet light damage from sunlight and other light sources, and pigments the skin and hair. Gray hair and/or depigmented skin are considered undesirable. Repigmentation of hair and skin is considered desirable by many persons socially and aesthetically. The formulation described herein is useful for repigmentation of hair and/or skin having deficient or non-functional melanocytes.

Pigment (melanin) is made by specialized cells (melanocytes). Pigment made in melanocytes is transferred to cells of the skin or hair. In a functioning melanocyte, melanin is synthesized and packaged in pigment organelles called melanosomes. A single melanocyte supplies melanosomes to its group of 36 associated keratinocytes. Melanosomes are transferred via dendrites (extensions) of the melanocyte.

A reservoir of melanocytes exists in hair follicles. When the hair follicular melanocytes are activated, hair and skin pigment. Thus a greater number of melanocytes present in the hair follicles lead to greater pigmentation in the skin and hair. Hypopigmentation of the skin and hair in humans and animals results from local defects in the melanin production within the melanocyte. It is now possible without harmful side effects to achieve normalization of hypopigmentation. Furthermore, it is now possible to achieve darkening of graying hair. It is believed that the active agents in the present formulation stimulate the proliferation of melanocyte cells, thus causing pigmentation of the skin surface and hair.

Synthesis of melanin within a melanocyte is controlled by the activity of an enzyme, tyrosinase, which is localized in an intracellular organelle—the premelanosome. Upon activation of tyrosinase, melanin is deposited with the organelle. After complete melanization, the premelanosome is known as a melanosome. Melanosomes are delivered to surrounding keratinocytes of the skin cells within the shaft of the graying hair by the process known as cytocrine secretion. Melanin synthesis occurs within the melanosomes in the presence of the oxidative enzyme tyrosinase, which converts tyrosine to dihydroxyphenylalaline (DOPA) and subsequently to DOPAquinone. Tyrosinase requires copper for oxidation of tyrosine to DOPA. Tyrosinase (and other members of the tyrosinase protein family) contains two atoms of copper per molecule; hence, a deficiency in copper prevents formation of DOPA. Furthermore, copper must be transported into the melanocytes and the melanosomes for their function. Copper requires the presence of pantothenic acid in order to be absorbed. As a result, copper and, to a lesser extent, pantothenic acid are key components of the current formulation. Copper can, however, deplete zinc in the body. Therefore, zinc can be added to the formulation to offset this.

Folic acid, another component of the current formulation, contains three components: pteridine, para-aminobenzoic acid, and L-glutamic acid. Free pteridine is the coenzyme for the enzymatic hydroxylation of phenylalanine to tyrosine. Thus a deficiency in folic acid, and hence pteridine, causes a deficiency in tyrosine, and hence, prevents formation of DOPA. Para-aminobenzoic acid (PABA) (a component of folic acid) is also needed for melanogenesis. PABA helps in the utilization of pantothenic acid, hence aiding copper absorption in the body. Thus, administering folic acid as a whole is more effective in stimulating pigment production than administering either pteridine or PABA alone.

Vitamin B12 deficiency can also affect vitiligo patients. First, folic acid and vitamin B12 require each other's presence in biological reactions. Reactions are accelerated by supplying the two vitamins together. Furthermore, taking folic acid without taking B12 will deplete the body's B12 supply and can also mask B12 deficiency. A deficiency in B12 can lead to a deficiency in folic acid and vice versa. Hence, taking them together is recommended. Also, one of the theories relating to loss of melanocytes in vitiligo involves nervous system disorders, resulting in an anomalous distribution of neuropeptides in vitiliginous skin. Vitamin B12 deficiency can result in defective synthesis of myelin, a key protein in the glial cells that insulate nerve cells. Thus, vitamin B12 can potentially aid in healing vitiligo by helping to repair defective nerve cells.

Vitamin C is needed for the complete metabolism of tyrosine, Phenylalanine, and dihydroxyphenylalanine. Vitamin C enhances the rate of transformation of tyrosine to dopa. Vitamin C is also needed for the metabolism of folic acid. Supplemental use of hydrochloric acid normalizes vitamin B12 and folic acid absorption, in cases of low or no stomach acid. Also, to have optimal absorption of vitamin C, adequate HCl is required. The vitamins and minerals taken in the present therapy must be available for use in the pigment production process. The vitamins and minerals must be ingested and absorbed in order to be used by the body. The ingestion of hydrochloric acid helps assure their absorption.

In all variations of the dosage regimen described herein, the efficacy of cutaneous repigmentation is enhanced by the optional exposure to sunlight or ultraviolet light. This is because exposure to sunlight or ultraviolet light can accelerate movement of melanosomes within melanocytes in skin. This exposure may be accomplished by brief periods of sunbathing a few times a week, or by treatment in a conventional tanning bed.

Thus the reader will see that the folic acid, vitamin B12, vitamin C, copper and pantothenic acid are the ingredients which support melanin production. Their consumption and absorption will cause more active melanin production. The current invention provides a safe, non toxic method of stimulating pigment production in depigmented hair and skin. Excess vitamins and minerals are excreted through urine; thus they do not build up to dangerous levels in the body. The melanin production process and hence repigmentation process can be enhanced by the addition of hydrochloric acid because it aids in vitamin absorption. Repigmentation of the skin can be accelerated by exposure to sunlight or ultraviolet light.

While my above description contains many specifics, these should not be construed as limitations on the scope of the invention, but rather as an exemplification of one preferred embodiment thereof. Many other variations are possible. For example, folic acid, vitamin B12, vitamin C, can be taken together without copper, but with sufficient pantothenic acid to aid in absorption of copper from the diet. Similarly, folic acid, vitamin B12, vitamin C, and pantothenic acid can be taken together without copper but with hydrocholoric acid. Folic acid, vitamin B12, vitamin C, pantothenic acid, and hydrochloric acid can be taken together daily, with 1 mg. of copper and 5 mg. of zinc taken every other day. Folic acid, vitamin C, pantothenic acid, hydrochloric acid may be taken daily, plus an injection of vitamin B12 administered weekly.

Alternatively, the composition can be administered topically. One method of doing this involves incorporation of the nutrients vitamin B12, copper, folic acid, vitamin C, and optionally pantothenic acid, zinc, and Betaine HCl into a makeup or suntan formulation for application to the skin of a patient with vitiligo.

The active ingredients of the current invention, vitamin B12, copper, folic acid, vitamin C, and optionally one or both of pantothenic acid and zinc, may be compounded into a topically applied formulation, such as a lotion or gel comprising the above ingredients and a liquid vehicle. The liquid vehicle may comprise water, alone or in combination with other solvents; water-soluble thickeners, such as hydrophilic polyacrylates, cationic polymers, and polyethylene glycols; insoluble thickeners, such as silicones and hydrophobic polyacrylates; and surfactants. Various oils and waxes may be dispersed or emulsified into the aqueous vehicle. The formulation may be applied as a liquid foundation makeup or as a suntan formulation. If the formulation is used as a makeup, dyes and pigments should be added to the formulation so as to cause the color of the formulation to match the color of normally pigmented skin. Other makeup formulations which include the active ingredients, such as products like lipstick or eyeshadow, may be used to color depigmented skin. A lipstick formulation for treating vitiligo might include, along with the active ingredients, such ingredients as assorted oils and waxes, such as sunflower oil, castor oil, beeswax, coconut oil, candelilla wax, cocoa butter, or carnauba wax; colorants, such as mica, titanium dioxide, iron oxide, or carmine; and assorted scents and nutrients, such as lanolin, peppermint oil, tocopheryl acetate and tocopherol (vitamin E), comfrey root extract, and rosemary extract. Penetration enhancers, such as glycerol, N-methyl-2-pyrrolidinone, laurocapram, and 1-menthol, may be added to the above makeup formulations to aid in carrying the active ingredients through the outer skin layers.

If the formulation is used as a suntan lotion to protect depigmented skin, suitable active agents should be added, such as zinc oxide, methoxycinnamic acid esters, and salicylic acid esters. Depending on the thickness of the formulation, it may be spread onto the skin as a cream or lotion, or sprayed onto the body. Penetration enhancers may be added to the formulations, to allow the active ingredients to more easily penetrate through the skin.

If desired, the active ingredients may also be included in a formulation for cleansing the skin, body, or hair. For example, the active ingredients may be added to a solid or liquid soap formulation, comprising one or more soaps (alkali metal salts of fatty acids), alone or in combination with other surfactants; water; thickeners; and other conventional ingredients. The active ingredients may also be used in skin cleansers, shampoos and conditioners comprising non-soap surfactants. These formulations may also include penetration enhancers to allow the active ingredients to penetrate the skin.

It is also contemplated to dissolve or disperse the active ingredients, vitamin B12, copper, folic acid, vitamin C, and optionally one or both of pantothenic acid and zinc, in an acrylic or isobutylene-based adhesive formulation. The adhesive formulation is then applied to a plastic or foil backing which is impermeable to the active ingredients, resulting in an adhesive patch which may be applied to a skin surface to allow transdermal administration of the active ingredients. Penetration enhancers are preferably included in the adhesive formulation. A release paper may be applied to the adhesive layer of the patch to protect the adhesive layer. Prior to use of the patch, the release paper is removed to expose the adhesive.

The formulation described in this document may also have utility in treatment of autoimmune disorders resulting in hair loss, such as Alopecia Areata. This treatment may be used by itself, or as a supplement to treatment with cyproterone-acetate and/or ethinyl-oestradiol. Copper compounds, including copper peptides, have been shown in clinical trials to stimulate hair follicles into their growth phase, effectively countering the damaging work of DHT (dihydrotestosterone). Many studies have demonstrated the positive effects of copper peptides on hair follicles. During the growth phase, the base of the hair follicle is richly endowed with substances such as collagen and various proteins. These substances are virtually absent during the resting phase. Copper has been shown to stimulate the cells responsible for production of these substances. Additionally, when cyproterone-acetate and/or ethinyl-oestradiol are used in treatment of Alopecia Areata, significant decreases in mean serum vitamin B12 may be observed. Supplementation of such conventional therapies with this invention allows stimulation of hair growth with copper, while simultaneously compensating for reduced levels of vitamin B12.

Accordingly, the scope of the invention should be determined not by the embodiments described, but by the appended claims and their legal equivalents.

What is claimed is:

1. A method of treating vitiligo, comprising the steps of:
   a) orally administering a composition comprising about 0.007-500 mg/day of vitamin B12 and about 0.7-3 mg/day of copper to a patient suffering from vitiligo;
   b) administering about 0.15-50 mg/day of folic acid to said patient; and
   c) administering about 15-1000 mg/day of vitamin C to said patient.

2. The method of claim 1, further comprising the step of:
   d) administering an effective amount of pantothenic acid and an effective amount of a hydrochloride salt to said patient.

3. The method of claim 1, further comprising the step of:
   d) administering an effective amount of zinc and an effective amount of a hydrochloride salt to said patient.

4. The method of claim 1, further comprising the step of:
   d) administering an effective amount of pantothenic acid, zinc, or a combination thereof to said patient.

5. The method of claim 1, wherein said vitamin B12, copper, folic acid, and vitamin C are compounded into a single tablet.

6. The method of claim 4, wherein said vitamin B12, copper, folic acid, vitamin C, pantothenic acid and zinc are compounded into a single tablet.

7. A method of restoring pigmentation of skin in a human patient in need thereof, comprising the step of administering a composition comprising 0.007-500 mg vitamin B12, 0.7-3 mg copper, 0.15-50 mg folic acid and 15-1000 mg vitamin C to said patient on a daily basis,
   wherein said vitamin B12, copper, folic acid, and vitamin C are compounded into a topically applied formulation.

8. The method of claim 7, wherein said topically applied formulation is selected from the group consisting of skin cream, skin lotion, soap, facial cleanser, shampoo, conditioner, and body spray.

9. The method of claim 7, further comprising the step of administering an effective amount of pantothenic acid, zinc, or a combination thereof to said patient, wherein said vitamin B12, copper, folic acid, vitamin C, and said effective amount of pantothenic acid, zinc, or a combination thereof are compounded into a topically applied formulation.

10. The method of claim 9, wherein said topically applied formulation is selected from the group consisting of skin cream, skin lotion, soap, facial cleanser, shampoo, conditioner, and body spray.

11. The method of claim 1, further comprising the step of administering an effective amount of hydrochloric acid to said patient.

12. The method of claim 4, further comprising the step of administering an effective amount of hydrochloric acid to said patient.

13. A method of restoring pigmentation of skin in a female patient in need thereof, comprising the steps of:
   a) on days when said female patient is not undergoing menses, administering a composition comprising an effective daily amount of 0.007-500 mg vitamin B12, an effective daily amount of 0.7-3 mg copper, an effective daily amount of 0.15-50 mg folic acid, and an effective daily amount of 15-1000 mg vitamin C to said female patient; and
   b) on days when said female patient is undergoing menses, administering an effective daily amount of 0.007-500 mg vitamin B12, an effective daily amount of 0.15-50 mg folic acid, and an effective daily amount of 15-1000 mg vitamin C to said female patient in the absence of copper supplementation.

14. The method of claim 13, further comprising the step of:
   c) administering an effective daily amount of both pantothenic acid and zinc to said female patient on both days when said female patient is undergoing menses and days when said female patient is not undergoing menses.

15. A method of restoring pigmentation of skin in a human patient in need thereof, comprising the steps of:
   a) orally administering a composition comprising an effective daily amount of 0.007-500 mg vitamin B12, an effective daily amount of 0.7-3 mg copper, an effective daily amount of 0.15-50 mg folic acid, and an effective daily amount of 15-1000 mg vitamin C to said patient; and
   b) exposing depigmented skin or hair of said patient to the sun or to ultraviolet light.

16. The method of claim 15, further comprising the step of:
   e) administering an effective amount of pantothenic acid, zinc, a hydrochloride salt, or a mixture thereof to said patient.

17. A method of restoring pigmentation of skin in a human patient in need thereof, comprising the steps of:
   a) orally or sublingually administering vitamin B12 to said patient in an amount of 0.007-500 mg/day; and
   b) orally administering a composition comprising 0.7-3 mg copper, 0.15-50 mg folic acid and 15-1000 mg vitamin C to said patient on a daily basis.

18. The method of claim 17, wherein said effective amount of vitamin B12 is administered orally.

19. The method of claim 17, further comprising the step of:
   c) administering an effective amount of pantothenic acid, zinc, a hydrochloride salt, or a mixture thereof to said patient.

20. The method of claim 17, further comprising the step of:
   c) exposing skin or hair of said patient to the sun or to ultraviolet light.

21. The method of claim 17, wherein said copper, folic acid, and vitamin C are compounded into a single tablet; and said vitamin B12 is administered sublingually.

* * * * *